United States Patent
Everett

[19]

[11] Patent Number: 6,019,482
[45] Date of Patent: Feb. 1, 2000

[54] POLYCHROMATIC BODY SURFACE IRRADIATOR

[76] Inventor: Randall L. Everett, 3817 SW. 15th St., Gainesville, Fla. 32608

[21] Appl. No.: 09/173,022

[22] Filed: Oct. 15, 1998

[51] Int. Cl.$^7$ ....................................................... F21L 7/00
[52] U.S. Cl. .......................... 362/184; 362/205; 362/231; 362/800
[58] Field of Search ..................................... 362/184, 205, 362/231, 800

[56] References Cited

U.S. PATENT DOCUMENTS

| | | | |
|---|---|---|---|
| D. 331,288 | 11/1992 | Yuen | D24/214 |
| D. 333,351 | 2/1993 | Tsou | D24/214 |
| D. 347,283 | 5/1994 | Von Winckler | D24/214 |
| 1,730,808 | 10/1929 | Croom . | |
| 4,825,868 | 5/1989 | Suza | 128/376 |
| 4,831,504 | 5/1989 | Nishizawa et al. | 362/100 |
| 5,413,587 | 5/1995 | Hochstein | 607/100 |
| 5,420,768 | 5/1995 | Kennedy | 362/119 |

OTHER PUBLICATIONS

"Color Medicine" by Charles Klotsche ISBN 929385–27–6 (Book 101 pages) (No Date).

*Primary Examiner*—James Phan
*Attorney, Agent, or Firm*—Alvin S. Blum

[57] ABSTRACT

A hand-held, self-contained irradiator is powered by batteries. At an applicator end are provided many diodes that emit electromagnetic radiation in the visible and/or infrared portions of the spectrum. A series of switches are provided so that the user may select which one or ones of the diodes to activate to provide particular wavelengths or colors of radiation to be emitted from the applicator end to be used to treat particular body surface areas for the relief of pain or other problems. An optional line cord powered embodiment is also disclosed.

8 Claims, 1 Drawing Sheet

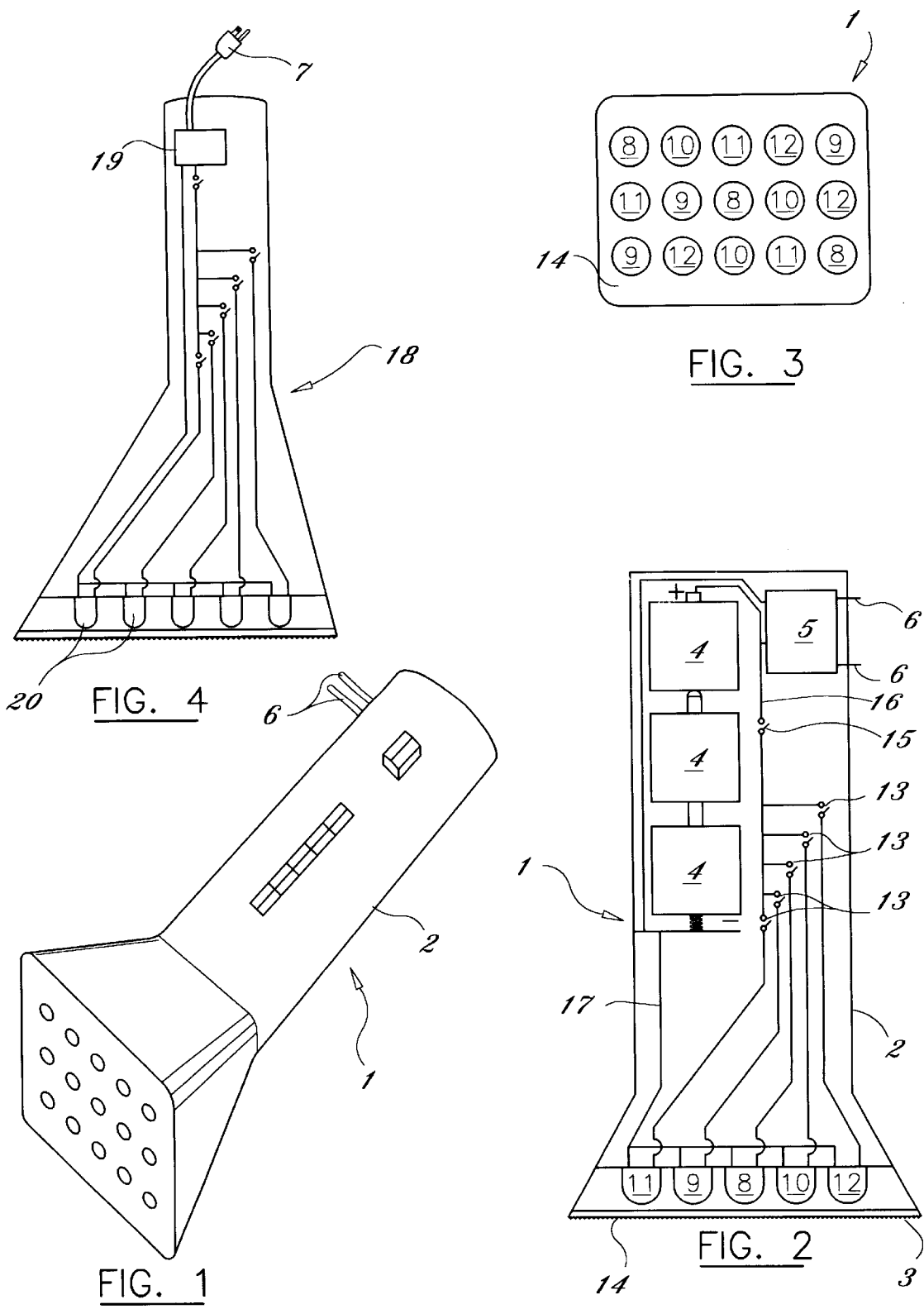

POLYCHROMATIC BODY SURFACE IRRADIATOR

BACKGROUND OF THE INVENTION

This invention relates to devices for irradiating the body with light of different colors.

Some alternative medicine proponents believe that particular colors of light, applied to the body surface at particular areas can relieve particular ailments. The light is generally provided by an incandescent bulb that passes through specific color filters. Since the light from an incandescent tungsten filament contains substantially all of the wavelengths of light, and only a very small fraction is desired for a particular purpose, most of the light is wasted. It is absorbed in the color filter and often it must be first passed through a heat shield filter to absorb some of the light energy to protect the color filters from deterioration. Most of the color filters employed for this purpose pass through a fairly broad band of wavelengths or colors, many of which may not be useful. Narrow band pass filters are available, but they are quite expensive. It would be useful to have a hand held device that could be selectively adjusted to provide light of particular wavelengths in which all of the electric power were used only for emitting the selected wavelengths.

SUMMARY OF THE INVENTION

The invention comprises a small, hand held housing that may be powered by a line cord or a self-contained battery that may be rechargeable. The housing contains a plurality of light emitting diodes (LED) oriented to emit light out of one end of the housing. The LEDs each emit light of a narrow band of frequencies. LEDs are provided with different wavelengths or color characteristics. Switches are provided on the housing for connecting selected one or ones of the LEDs to the electric power in series with an on/off switch. By this means, a single hand held device can be used to irradiate the body surface at small selected areas with many selected narrow bandwidths or colors, and the user can change colors by simply changing the switch settings. Because substantially all of the electric power consumed by an LED is converted to light of a narrow bandwidth, there is very little wasted energy consumption and heating of the device.

These and other objects, advantages and features of the invention will become more apparent when the detailed description is studied in conjunction with the drawings.

BRIEF DESCRIPTION OF THE DRAWINGS

FIG. 1 is a perspective view of an irradiator of the invention.

FIG. 2 is a schematic view of the irradiator.

FIG. 3 is an end view of the irradiator of FIG. 1.

FIG. 4 is a schematic view of another embodiment of the invention.

DETAILED DESCRIPTION OF PREFERRED EMBODIMENTS

Referring now to the FIGS. 1–3, the self-contained, hand-held irradiator 1 comprises a light plastic housing 2 having an applicator end 3 which will normally be placed on the skin surface at the selected area that is to be treated, such as for pain relief and other problems that are to be alleviated by radiation treatment. Contained within the housing are rechargeable batteries 4 that are recharged by battery charger 5 by plugging contacts 6 into a wall outlet. The positive lead 16 from the batteries is connected through an on/off switch 15 to multiple selector switches 13 and then to the anodes of the following electromagnetic radiation emitting diodes with their wavelengths 8 infra red 840 nm
9 red 660 nm
10 yellow 595 nm
11 green 565 nm
12 orange 620 nm There are three of each wavelength connected in parallel. The cathodes are wired by common cathode lead 17 to the negative side of the battery power means 4. The operator selects which one or ones of the wavelengths desired by closing the respective switches. Then activating the on/off switch 15 causes the visible or infrared radiation to pass through the applicator end 3 which may be provided with a diffusing lens 14 to spread the radiation more uniformly.

The term polychromatic refers to the many colors that may be selected to irradiate the skin surface. These diodes are small in size. Although the example illustrated provides a choice of only five different wavelengths, many more wavelength choices may be provided in a single unit, such as, for example, but not limited to, the following wavelengths: 940, 880, 840, 700, 660, 655, 645, 635, 620, 595, 585, 568, 565, and 470 nanometers.

Referring now to FIG. 4, another embodiment 18 of the invention is shown in which electric power to the diodes 20 is provided by power supply 19 through line cord 7 that plugs into an ordinary electrical wall outlet.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention.

What is claimed is:

1. A skin surface irradiator for relief of pain and other ailments comprising:
   A) a housing having an applicator end;
   B) power means within the housing for providing electric power including a battery or electric line cord;
   C) a plurality of light emitting diodes (LED) within the housing positioned to emit light out the applicator end, the LEDs selected to emit a plurality of different colors or wavelengths for relief of pain and other ailments;
   D) selective switch means on the housing for selectively connecting to the power means one or more of the LEDs of different colors; and
   E) on/off switch means interposed between the power means and the selective switch means for activating and deactivating the LEDs.

2. The irradiator according to claim 1 further comprising a light diffuser in the path of the light emitted from the LEDs to spread the emitted light over a broader path.

3. The irradiator according to claim 2, in which the power means comprises a rechargeable battery and battery recharger.

4. A skin surface irradiator for relief of pain and other ailments comprising:
   A) a hand-held, self-contained housing having an applicator end;

B) electric battery means contained within the housing for powering electromagnetic radiation emitting diodes;

C) a plurality of electromagnetic radiation emitting diodes in the housing positioned to emit radiation out the applicator end, the diodes constructed to emit radiation of at least three different wavelengths in the visible or infrared portions of the electromagnetic spectrum for relief of pain and other ailments;

D) selective switch means on the housing for selectively connecting to the battery means one or more of the diodes so as to emit one or more different wavelengths; and E) on/off switch means interposed between the selective switch means and the battery means for activating and deactivating the selected diodes.

5. The irradiator according to claim 4 further comprising a diffuser in the path of the radiation to spread the emitted radiation over a broader path.

6. The irradiator according to claim 5, in which the housing further contains means for recharging the battery means.

7. The irradiator according to claim 4, in which the at least three wavelengths are selected from the group of wavelengths consisting of 940, 880, 840, 700, 660, 655, 645, 635, 620, 595, 585, 568, 565, and 470 nanometers.

8. A method of treating body skin surfaces for relief of pain and other ailments comprising:

1) providing a skin surface irradiator comprising:
   A) a hand-held, self-contained housing having an applicator end;
   B) electric battery means contained within the housing for powering electromagnetic radiation emitting diodes;
   C) a plurality of electromagnetic radiation emitting diodes in the housing positioned to emit radiation out the applicator end, the diodes constructed to emit radiation of at least three different wavelengths in the visible or infrared portions of the electromagnetic spectrum for relief of pain and other ailments;
   D) selective switch means on the housing for selectively connecting to the battery means one or more of the diodes so as to emit one or more different wavelengths; and
   E) on/off switch means interposed between the selective switch means and the battery means for activating and deactivating the selected diodes;

2) selecting particular wavelength or wavelengths with the selective switch means;

3) applying the applicator end to the skin surface to be treated; and 4) operating the on/off switch means.

* * * * *